(12) United States Patent
Liu et al.

(10) Patent No.: US 10,098,372 B2
(45) Date of Patent: Oct. 16, 2018

(54) WHITENING COMPOSITION AND THE USE THEREOF

(71) Applicant: INFINITUS (CHINA) COMPANY LTD, Jiang Men (CN)

(72) Inventors: Shuo Liu, Jiang Men (CN); Xiaoling Wang, Jiang Men (CN); Yiting Yang, Jiang Men (CN); Yan Zhong, Jiang Men (CN); Sheng Chen, Jiang Men (CN); Xiaowei Li, Jiang Men (CN)

(73) Assignee: INFINITUS (CHINA) COMPANY LTD, Jiang Men (CN)

( * ) Notice: Subject to any disclaimer, the term of this patent is extended or adjusted under 35 U.S.C. 154(b) by 20 days.

(21) Appl. No.: 15/126,054

(22) PCT Filed: May 6, 2016

(86) PCT No.: PCT/CN2016/081234
§ 371 (c)(1),
(2) Date: Sep. 14, 2016

(87) PCT Pub. No.: WO2016/192507
PCT Pub. Date: Dec. 8, 2016

(65) Prior Publication Data
US 2017/0172183 A1    Jun. 22, 2017

(30) Foreign Application Priority Data
Jun. 2, 2015   (CN) .......................... 2015 1 0295294

(51) Int. Cl.
*A23L 2/52*       (2006.01)
*A23L 33/105*   (2016.01)
(Continued)

(52) U.S. Cl.
CPC ................. *A23L 2/52* (2013.01); *A23C 9/156* (2013.01); *A23G 1/48* (2013.01); *A23G 3/48* (2013.01);
(Continued)

(58) Field of Classification Search
CPC   A23G 1/48; A23G 3/48; A23L 33/105; A23L 33/125
(Continued)

(56) References Cited

U.S. PATENT DOCUMENTS

2006/0257351 A1   11/2006  Chiba
2009/0028969 A1    1/2009  Sene et al.

FOREIGN PATENT DOCUMENTS

CN         1840145        10/2006
CN       101507698         8/2009
(Continued)

OTHER PUBLICATIONS

Asl et al., "Review of pharmacological effects of *Glycyrrhiza* sp. and its bioactive compounds," *Phytother. Res.*, 22(6):709-724, 2008.

(Continued)

*Primary Examiner* — Helen F Heggestad
(74) *Attorney, Agent, or Firm* — Parker Highlander PLLC (57) ABSTRACT

The present invention discloses a composition having whitening and brightening effect and the use thereof, the composition comprising: 1) Osmanthus; 2) Olive; and 3) *PUERARIAE LOBATAE RADIX, PLATYCODONIS RADIX, GLYCYRRHIZAE RADIX ET RHIZOMA, SIRAITIAE FRUCTUS* and *ANGELICAE DAHURICAE RADIX*. The composition may be applied to food products. Raw materials used in the composition of the present invention are all common food ingredients and have high safety. Unlike skin whitening products for external use, the composition is eaten (Continued)

as ordinary food, and has the skin whitening and brightening effect all over the body after being eaten. In addition, the composition of the present invention has a natural flower aroma of osmanthus fragrans flower, and a refreshing mouthfeel. The composition has gentle drug properties and is suitable for people with different constitutions. The composition contains a large amount of functional factors of polyphenols and has a health-care function for organism, and not only can whiten and brighten skins but also can enhance the anti-oxidative damage capacity of the organism.

11 Claims, 2 Drawing Sheets

(51) Int. Cl.
    *A23C 9/156*     (2006.01)
    *A23G 1/48*     (2006.01)
    *A23G 3/48*     (2006.01)
    *A23L 33/125*     (2016.01)

(52) U.S. Cl.
    CPC ........... *A23L 33/105* (2016.08); *A23L 33/125* (2016.08); *A23V 2002/00* (2013.01)

(58) Field of Classification Search
    USPC ........................................ 426/615, 648, 599
    See application file for complete search history.

(56) References Cited

FOREIGN PATENT DOCUMENTS

| | | |
|---|---|---|
| CN | 101972241 | 2/2011 |
| CN | 102670436 | 9/2012 |
| CN | 102836341 | 12/2012 |
| CN | 103876150 | 6/2014 |
| CN | 104013667 | 9/2014 |
| CN | 104042516 | 9/2014 |
| CN | 104206629 | 12/2014 |
| CN | 104886593 | 9/2015 |

OTHER PUBLICATIONS

Costa et al., "Association of emblica, licorice and belides as an alternative to hydroquinone in the clinical treatment of melisma," *An. Bras. Dermatol.*, 85(5):613-20, 2010.

Daqiang et al., "Inhibition of Extracts from Angelica Dahurica on Tyrosinase in vitro," *China Pharmacist*, 15(4):457-459, 2012. (English abstract of Chinese publication).

Ebanks et al., "Mechanisms Regulating Skin Pigmentation: The Rise and Fall of Complexion Coloration," *Int. J. Mol. Sci.*, 10:4066-4087, 2009.

English translation of PCT International Search Report issued in International Application No. PCT/CN2016/081234, dated Aug. 3, 2016.

Gao, "The analysis of different concentrations of angelica dahurica whitening lotion on human tyrosinase activity inhibition," *Chinese Herbal Medicine*, 38(38):373, 2015. (English summary of Chinese publication).

Gui et al., "Whitening effect of flavonoid materials in Radix puerariae," *China Surfactant Detergent & Cosmetics*, 43(4):290-312, 2013.

Guo et al., "Studying on whitening effect of Botanicals and Compounds," *Journal of Jiangxi University of Traditional Chinese Medicine*, 20(4):65-66, 2008. (English abstract of Chinese publication).

He, "The Cause of Freckle Formation," *The Book of Freckle Whitening Beauty*, pp. 206, 2014. (English summary of Chinese publication).

Hung et al., "The Ethanol Extract of Osmanthus fragrans Flowers Reduces Oxidative Stress and Allergic Airway Inflammation in an Animal Model," *Evidence-Based Complementary and Alternative Medicine*, vol. 2013, Article ID 304290, 10 pages, 2013.

Jin, "A preliminary study and Application of kudzu root in Cosmetics," *Chinese Wild Plant Resources*, 3:11-13, 2000. (English abstract of Chinese publication).

Jung et al., "Depigmenting action of platycodin D depends on the cAMP/Rho-dependent signalling pathway," *Exp. Dermatol.*, 12:986-991, 2011.

Kasamatsu et al., "The inhibitory effect of a Platycodon root extract on ultraviolet B-induced pigmentation due to a decrease in Kit expression," *J. Nat. Med.*, 68:643-646, 2014.

Li and Wang, "New recognition and biological research progresses of skin pigmentation," *Chinese Journal of Aesthetic Medicine*, 18(9):1372-1375, 2009. (English concise explanation of the relevant of Chinese publication).

Liu, "Olives," *The Book of Diabetes Diet Quick Check*, p. 82, 2013. (English summary of Chinese publication).

Office Communication issued in Chinese Patent Application No. 201510295294.X, dated Aug. 3, 2016. (English translation of Chinese publication).

Office Communication issued in Chinese Patent Application No. 201510295294.X, dated Feb. 4, 2017. (English translation of Chinese publication).

Tang and Zhao, "Research progress on chemical constituents of plants from *Osmanthus* L. and other their pharmacology," *Chinese Herbal Medicine*, 45(4):590-602, 2014. (English concise explanation of relevance of Chinese publication).

Zhan, "There are several Chinese medicine beauty and beautiful skin," *China Health Nutrition*, 3:49, 2005. (English summary of Chinese publication).

Zhong et al., "Inhibitory Effect of Active Constituents from Radix Puerariae on Tyrosinase," *Nat. Prod. Res. Dev.*, 20:681-684, 2008. (English abstract of Chinese publication).

WHITENING COMPOSITION AND THE USE THEREOF

CROSS REFERENCE OF RELATED APPLICATIONS

The present application is a national phase application under 35 U.S.C. § 371 of International Application No. PCT/CN2016/081234, filed May 6, 2016, which claims the benefit of priority to Chinese Patent Application No. 201510295294.X, filed Jun. 2, 2015 and entitled "WHITENING COMPOSITION AND THE USE THEREOF," the entirety of each of which is incorporated herein by reference.

FIELD OF THE INVENTION

The present invention relates to a composition and its applications, particularly relates to a composition having whitening and brightening effects and its application.

BACKGROUND OF THE INVENTION

Beauty of traditional Chinese medicine is based on the guidance of the basic theory of traditional Chinese medicine and traditional Chinese aesthetics, which prevents and controls diseases that damage beauty by oral or topical administration of traditional Chinese herbal medicine so as to obtain a cosmetic method and basic means for realizing nourished face and pleasant look.

The human skin color is determined by melanocytes and melanin levels generated therefrom in the outermost layer of skin, i.e. the epidermis. The increase of melanin content in skin is related to the enhanced activity of melanocytes, whereas ultraviolet radiation in the sunlight is the main cause of the increase in melanin synthesis (Chengxin Li, Ling Wang. Research progress in generative mechanism of skin pigmentation [J]. Chinese Journal of Aesthetic Medicine, 2009, 09: 1372-1375).

Melanin is synthesized in melanocytes by enzymatic reaction and then released into the epidermis, and is eliminated along with the process of epidermis replacement. The depth of skin color is related to the activity of melanocytes, synthesis rate of melanin, eliminating rate of melanin (Mechanisms Regulating Skin Pigmentation: The Rise and Fall of Complexion Coloration, Int. J. Mol. Sci. 2009, 10, 4066-4087).

At present, although the prior art discloses a number of whitening formula, as in the following two patents:

China Patent CN201210064589.2 "Whitening anti-aging cosmetic containing *cistanche tubulosa* extract and preparation method thereof" discloses a whitening anti-aging cosmetic whose main raw material is *cistanche tubulosa* extract. In the extract, the content of echinacoside is ≥25%, and the content of verbascoside is ≥55%. This patent discloses a whitening anti-aging cosmetic for external use whose main functional components are echinacoside and verbascoside. Whitening active ingredients such as echinacoside and verbascoside have poor stability when used externally in cosmetics as the matrix is generally basic; active ingredients have poor transdermal absorption when used externally, which compromises the whitening effect.

China Patent CN201210368849.5 "Medicinal instant granules having whitening effect and preparation method thereof", discloses medicinal instant Granules prepared from radix paeoniae alba, rose flower, Chinese honeylocust spine, radix saposhnikoviae, rhizoma polygonati, *GLYCYRRHIZAE RADIX ET RHIZOMA*, mulberry, ginseng flowers, heterophylla, semen zizyphi spinosae, concrete of dahurian rose fruit, vitamin C, vitamin E, arbutin, grape seed extract and excipients, which have effects of inhibiting melanin and whitening skin. In accordance with the provisions of Ministry of Health, raw materials of Chinese honeylocust spine and radix saposhnikoviae are not available for ordinary food and heal-care food, so there is a big safety risk.

From the foregoing, the formulae in the above patents all have deficiencies. Therefore, an urgent need for further research on whitening formula exists, in the hope of developing whitening formulae having better stability, better safety and improved effect.

SUMMARY OF THE INVENTION

The technical problem to be solved by the present invention is to provide a composition having whitening and brightening effect and the use thereof. The composition is an all-natural, safe, mouth-refreshing composition having skin whitening and brightening effect and is used in food area, etc.

To solve the above technical problem, the composition of the present invention having whitening and brightening effect (skin whitening and brightening) comprises:
1) *Osmanthus*;
2) Olive; and
3) *PUERARIAE LOBATAE RADIX, PLATYCODONIS RADIX, GLYCYRRHIZAE RADIX ET RHIZOMA, SIRAITIAE FRUCTUS* and *ANGELICAE DAHURICAE RADIX*.

Further, the useful forms of the *Osmanthus* include: powder or extract of *Osmanthus*; the useful forms of the Olive include: powder or extract of Olive fruit; the useful forms of the *PUERARIAE LOBATAE RADIX, PLATYCODONIS RADIX, GLYCYRRHIZAE RADIX ET RHIZOMA, SIRAITIAE FRUCTUS* and *ANGELICAE DAHURICAE RADIX* include: crude drugs of *PUERARIAE LOBATAE RADIX, PLATYCODONIS RADIX, GLYCYRRHIZAE RADIX ET RHIZOMA, SIRAITIAE FRUCTUS* and *ANGELICAE DAHURICAE RADIX*, or the total extract of *PUERARIAE LOBATAE RADIX, PLATYCODONIS RADIX, GLYCYRRHIZAE RADIX ET RHIZOMA, SIRAITIAE FRUCTUS* and *ANGELICAE DAHURICAE RADIX*; in the composition, parts by weight of each of the components are preferably 1 part to 10 parts of *Osmanthus*, 0.1 parts to 1 part of Olive, 10 parts to 50 parts of *PUERARIAE LOBATAE RADIX*, 10 parts to 20 parts of *PLATYCODONIS RADIX*, 1 part to 10 parts of *GLYCYRRHIZAE RADIX ET RHIZOMA*, 1 part to 20 parts of *SIRAITIAE FRUCTUS*, 1 part to 10 parts of *ANGELICAE DAHURICAE RADIX*.

Further, the ingredients of Olive and *Osmanthus* in the composition are dried powder of juice or extract, or original liquor of juice or extract, concentrate of juice or extract or enriched material of active ingredients; the *PUERARIAE LOBATAE RADIX, PLATYCODONIS RADIX, GLYCYRRHIZAE RADIX ET RHIZOMA, SIRAITIAE FRUCTUS* and *ANGELICAE DAHURICAE RADIX* are in the form of crude drugs or dried power, or concentrate of extract or enriched material of active ingredients; the powder of *Osmanthus* includes: the powder obtained by pulverizing the dried flowers of *osmanthus fragrans*; the extract of *Osmanthus* includes: the extract obtained by mixing *Osmanthus* with water, alcohol or one or several types of other food processing aids; the powder of Olive fruit includes: powder obtained by pulverizing the Olive fruit or drying the juice of Olive fruit; the extract of the Olive fruit includes: the extract obtained by mixing Olive fruit with water, alcohol or one or several types of other food processing aids.

Further, the total extract of PUERARIAE LOBATAE RADIX, PLATYCODONIS RADIX, GLYCYRRHIZAE RADIX ET RHIZOMA, SIRAITIAE FRUCTUS and ANGELICAE DAHURICAE RADIX includes: the extract obtained by mixing PUERARIAE LOBATAE RADIX, PLATYCODONIS RADIX, GLYCYRRHIZAE RADIX ET RHIZOMA, SIRAITIAE FRUCTUS and ANGELICAE DAHURICAE RADIX with water, alcohol or one or several types of other food processing aids.

Further, the composition further comprises: one or more of food ingredients, food additives, fruit juice, fruit powder.

Further, the composition may further comprise: one or more of food ingredients, food additives, fruit juice, fruit powder.

Further, the food ingredients may be a variety of conventional food ingredients, such as including: one or more of white sugar, non-dairy creamer, malt dextrin, tea powder (such as instant tea powder) and the like; wherein the weight ratio of food ingredients to Osmanthus is 1-50: 1-10 (e.g. the parts by weight of food ingredients are 1-50 parts, those of Osmanthus are 1-10 parts).

The food additives may be a variety of conventional food additives, such as including: one or more of citric acid and sodium salt or potassium salt thereof, vitamin C, vitamin E, stevioside and the like; wherein the weight ratio of food additives to Osmanthus is 0.1-2: 1-10 (e.g. the parts by weight of food additives are 0.1-2 parts, those of Osmanthus are 1-10 parts).

The fruit juice may be a variety of conventional fruit juices, such as including: one or more of apple juice, grape juice, black currant juice, sugar cane juice, orange juice; the fruit juice also includes various conventional concentrated fruit juice, such as including: one or more of concentrated apple juice, concentrated grape juice, concentrated black currant juice, concentrated sugarcane juice, concentrated orange juice; that is to say, in the present invention, the fruit juice can be various unconcentrated or concentrated fruit juice, including one or more of apple juice, grape juice, black currant juice, sugar cane juice, orange juice; or one or more of concentrated apple juice, concentrated grape juice, concentrated black currant juice, concentrated sugarcane juice, concentrated orange juice; in addition, the weight ratio of the fruit juice to Osmanthus is 10-50: 1-10 (e.g. the parts by weight of fruit juice are 10-50 parts, those of Osmanthus are 1-10 parts).

The fruit powder may be a variety of conventional fruit powder, such as including: one or more of apple fruit powder, grape fruit powder, black currant fruit powder, mango fruit powder, mulberry fruit powder; wherein the weight ratio of fruit powder to Osmanthus is 10-50: 1-10 (e.g. the parts by weight of fruit powder are 10-50 parts, those of Osmanthus are 1-10 parts).

Further, the present invention also provides a method for preparing the above-mentioned composition having whitening and brightening effect, comprising:

mixing the Osmanthus, Olive and PUERARIAE LOBATAE RADIX, PLATYCODONIS RADIX, GLYCYRRHIZAE RADIX ET RHIZOMA, SIRAITIAE FRUCTUS and ANGELICAE DAHURICAE RADIX, and then preparing them into the composition.

Further, the crude drugs of PUERARIAE LOBATAE RADIX, PLATYCODONIS RADIX, GLYCYRRHIZAE RADIX ET RHIZOMA, SIRAITIAE FRUCTUS and ANGELICAE DAHURICAE RADIX are all in line with the requirements of Chinese Pharmacopoeia 2010 version. The dosage forms of the composition include: a variety of oral preparations.

Further, in the above-mentioned preparation method, one or more of the above-mentioned food ingredients, food additives, fruit juice, fruit powder and the like may be further added, and then preparing the various ingredients into formulations of the composition (corresponding formulations).

Furthermore, the present invention also provides a use of the above-mentioned composition having whitening and brightening effect, such as a use of the composition in the preparation of food or health products having whitening and brightening effect.

The food or health products include: liquid food or health products, or solid, semi-solid food or health products;

wherein the liquid food or health products include: beverages, oral liquid or milk;

the solid or semi-solid food or health products include: biscuits, pastries, instant granules, candies, chocolates, jelly, jam, canned food, gels and the like.

The main active ingredients in the composition of the present invention are polyphenols, and the final polyphenols content is ≥100 mg/100 ml.

The effects of the components involved in the present invention are as follows:

Osmanthus are dried flowers of edible flowers osmanthus fragrans. Compendium of Materia Medica: osmanthus flowers are spicy, warm, non-toxic; when prepared into a cake with Chinese gall leaven and catechu and hold in the mouth, the Osmanthus can help to promote the secretion of saliva or body fluid, deodorize and reduce phlegm, and treat carious pain. They are steamed with sesame oil, nourished, and prepared into facial grease. Chinese Materia Medica: spicy, warm. Distributed to the lung, spleen, kidney meridians. The effect ingredients of Osmanthus are plant polyphenols; the antioxidant and anti-inflammatory effects thereof are mostly reported in literature (The Ethanol Extract of Osmanthus fragrans Flowers Reduces Oxidative Stress and Allergic Airway Inflammation in an Animal Model Evidence-Based Complementary and Alternative Medicine. Volume 2013 (2013), Article ID 304290, 10 pages).

Olive is the dry ripe fruit of a medicine-food homologous plant from burseraceae family Olive Raeusch. Olive Raeusch is mild natured, sweet, sour, astringent, distributed to lung and stomach meridians. Modern research shows that the extract thereof has anti-aging and skin whitening activity (WO 01/026670).

PUERARIAE LOBATAE RADIX is the dried root of a medicine-food homologous plant from legume family Puerarialobata (Willd.) Ohwi. PUERARIAE LOBATAE RADIX is sweet, spicy, cool; distributed to spleen, stomach, lung meridians; it relieves muscles to expel heat, help to promote the secretion of saliva or body fluid and quench thirst, outthrust rashes, invigorates yang and is antidiarrheic, dredges meridians and activates collaterals, relieves alcloholism. The Shennong herbs: it is listed as middle grade of medicines; sweet, mild natured. It mainly treats diabetes, severe body heat, vomiting, various arthromyodynia, promotes yinqi, and detoxifies various toxins. Compendium of Materia Medica: sweet, spicy, mild natured, non-toxic. Dismissing the stagnant fire. Puerarin its main functional ingredient, which has a protective effect on UV-induced cell injury in epidermis and has an inhibitory effect on melanin synthease (Hui Gui, Ting Tang, Hang Yan, Zhijun Lei. Study on whitening effect of flavonoids of PUERARIAE LOBATAE RADIX [J]. Riyong Huaxue Gongye, 2013, 04: 290-293, 312).

PLATYCODONIS RADIX is the dried root of a medicine-food homologous plant from Campanulaceae family Platy-

*codongrandiflorum* (Jacq.) A.DC. It is mild natured, bitter, spicy, distributed to lung meridian. Modern pharmacological studies have shown that platycodin D can inhibit melanin synthesis and inhibits the release of melanin into the epidermis (Jung E, Hwang W, Kim S, Kim Y S, Kim Y S, Lee J, Park D. Depigmenting action of platycodin D depends on the cAMP/Rho-dependent signalling pathway. Exp Dermatol 2011 December; 20 (12): 986-91). Alcoholic extract of PLATYCODONIS RADIX has inhibitiory effect on the increase in skin pigment synthesis induced by UVB (Shinya Kasamatsu, Akira Hachiya, YoshieShimotoyodome, Akiyo Kameyama, Yuki Miyauchi, Kazuhiko Higuchi, Taketoshi Fujimori, Atsushi Ohuchi, Yusuke Shibuya, Takashi Kitahara. The inhibitory effect of a Platycodon root extract on ultraviolet B-induced pigmentation due to a decrease in Kit expression. J Nat Med (2014) 68: 643-646).

GLYCYRRHIZAE RADIX ET RHIZOMA is the dried root and rhizome of a medicine-food homologous plant from legume family *Glycyrrhizauralensis* Fisch. It is mild natured, sweet, distributed to heart, lung, spleen and stomach meridians. It tonifies the spleen and qi, clears away heat and toxic materials, coordinates the drug actions of a prescription, functions as the adjuvant drug in a prescription. Glabridin contained therein is a commonly used topical skin whitening agent (Asl M N, Hosseinzadeh H. Review of pharmacological effects of Glycyrrhizasp and its bioactive compounds. Phytother Res. 2008 June; 22 (6): 709-24).

SIRAITIAE FRUCTUS is the dried fruit of a plant from Cucurbitaceae family MomordicagrosvenoriSwingle. SIRAITIAE FRUCTUS is cool, sweet, distributed to lung, large intestine meridians.

ANGELICAE DAHURICAE RADIX is the dried root of a plant from Umbelliferae family ANGELICAE DAHURICAE RADIX (Fisch.exHoffm.) Benth.et Hook.f. ANGELICAE DAHURICAE RADIX is warm, spicy, distributed to lung, stomach, large intestine meridians. Modern studies suggest that its extract has the effect of inhibiting tyrosinase (Daqiang Hu, Lina Hou, Ruoqiu Fu, Desheng Meng, Hongyu Song, Mingfeng Xiang, Jing Xu Inhibitory effect of the extract of ANGELICAE DAHURICAE RADIX on tyrosinase in vitro [J]. *China Pharmacist*, 2012, 04: 457-459).

Compounding of fructus phyllanthi and PUERARIAE LOBATAE RADIX is useful for preparing ointment for external use. Fructus phyllanthi can enhance the topical whitening effect of PUERARIAE LOBATAE RADIX (Costa A, Moises T A, Cordero T, Alves C R, Marmirori J. Association of emblica, GLYCYRRHIZAE RADIX ET RHIZOMA and belides as an alternative to hydroquinone in the clinical treatment of melasma. An Bras Dermatol. 2010 September-October; 85 (5): 613-20).

According to the actions of the above-mentioned components, the aim of the present invention is to develop a natural, safe, mounth-refreshing food having the skin whitening and brightening function by selecting medicine-food homologous herbal raw materials based on the theory of traditional Chinese medicine.

Unlike achieving the skin whitening and brightening function by using the respective herbs alone, the present invention relates to a composition having skin whitening and brightening effect, said composition is obtained by compounding the extracts of *Osmanthus*, Olive and PUERARIAE LOBATAE RADIX, PLATYCODONIS RADIX, GLYCYRRHIZAE RADIX ET RHIZOMA, SIRAITIAE FRUCTUS and ANGELICAE DAHURICAE RADIX on the basis of traditional Chinese medicine theory. Yellow emperor's Canon of Medicine: Lung is the basis of qi, the hua thereof is in the hair, the chong thereof is in the skin. Lung dominates skin and hair. Heart is the basis of life, the hua thereof is in the face, the chong thereof is in the blood vessel in which the blood and qi circulate. Heart dominates the blood vessel in which the blood and qi circulate. In the prescription, PUERARIAE LOBATAE RADIX clears away heat and relieves exterior syndrome, invigorates yang and promotes blood circulation, moistens the lung and promotes the secretion of saliva or body fluid, functions as the principal drug; PLATYCODONIS RADIX opens the inhibited lung-energy, discharges pus, and activates qi and promotes blood circulation, while *Osmanthus* warm the stomach and dissipate stasis, warm the lung and promote the secretion of saliva or body fluid, both of the two drugs contribute to the enhancement of the effect of smoothing qi, blood and meridians of the prescription and function as ministerial drugs; SIRAITIAE FRUCTUS clears away heat and moistens the lung, moistens the bowel and defaecates, while GLYCYRRHIZAE RADIX ET RHIZOMA tonifies the qi and nourishes the heart, clears away heat and toxic materials, both of the two drugs contribute to the enhancement of the effect of moistening the lung and expelling toxic materials of the prescription and function as adjuvant drugs; the addition of a small amount of ANGELICAE DAHURICAE RADIX serves to provide aroma and free the orifices, dissipate wind and eliminate dampness, reduce swelling and drain pus, and functions as conductant drug. The combined use of these drugs produces the effects of invigorating yang and promoting blood circulation, opening the inhibited lung-energy and discharging pus, clearing away heat and reducing swelling, moistening the lung and promoting the secretion of saliva or body fluid all together, is capable of improving facial microcirculation, so as to remove the old waste keratin from the surface of the skin internally, and achieve the effects of smoothing qi and blood, moisturizing and whitening and brightening the skin.

Experiments prove that, after compounding *Osmanthus*, Olive and PUERARIAE LOBATAE RADIX, PLATYCODONIS RADIX, GLYCYRRHIZAE RADIX ET RHIZOMA, SIRAITIAE FRUCTUS and ANGELICAE DAHURICAE RADIX, the composition of the present invention can produce stronger skin whitening and brightening effect, and have synergistic skin whitening and brightening effect.

The raw materials used in the composition of the present invention are all common food raw materials, have high safety, are useful in a suitable and safe method for producing skin whitening and brightening effect, and can be consumed for a long term as ordinary food. Unlike topical skin whitening products, the composition is consumed as ordinary food; after consumption, it can produce skin whitening and brightening effect over the whole body, i.e. the effect can be reflected in the face, skin of various body parts, such as limbs, neck, back, etc., and has protective effect against on the sun tanning caused by sun burn. In addition, the composition of the present invention has a natural floral fragrance from *Osmanthus*, and a refreshing taste. The composition is mild in temperament and is suitable for consumption by people of various body constitutions. The composition contains large amounts of functional factors such as polyphenols, has a health care function for body, and can improve the capacity of anti-oxidative damage of the body while exerting the whitening and brightening skin effect.

DESCRIPTION OF THE DRAWINGS

The present invention will be further described in detail in conjunction with the accompanying figures and specific embodiments.

DETAILED EMBODIMENTS

Figure 1:
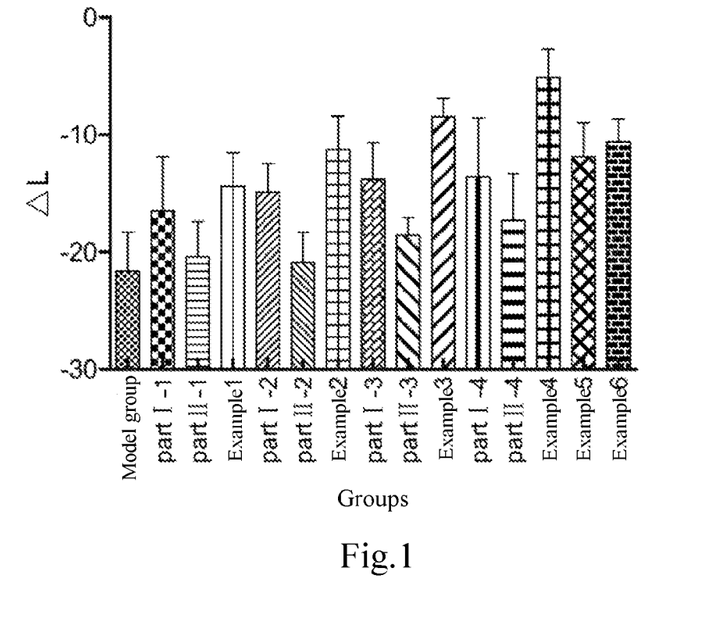
FIG. 1 is the effects of various formulae and examples on the reduction of brightness of guinea pig skin irradiated by ultraviolet.
Figure 2:
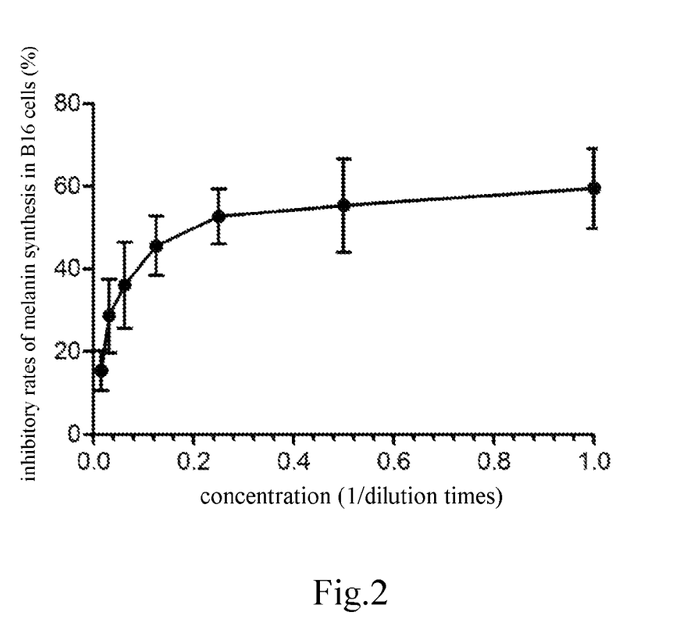
FIG. 2 is the inhibitory rates of Example 2 on melanin synthesis of melanoma cells from B16 mice.
Figure 3:
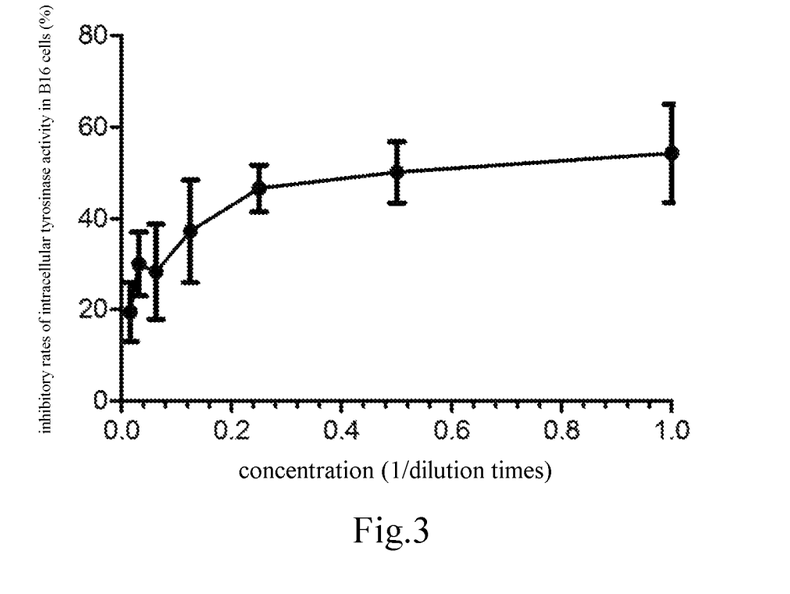
FIG. 3 is the inhibitory rates of Example 2 on tyrosinase of melanoma cells from B16 mice.

In the following examples, unless otherwise specified, the involved materials, reagents and the like are commercial products.

The First Embodiment

In the first embodiment, powder of *Osmanthus* (purchased from Huangshan Greenxtracts Co., Ltd.) is a solid prepared from aqueous extraction of dried flowers of the edible *Osmanthus*, with a polyphenol content of 120 mg/g, a lot number of 140301.

In the first embodiment, powder of Olive fruit (purchased from Guilin Layn Natural Ingredients Corp.) is a solid prepared from alcoholic extraction (60 v/v % enthanol) of the dry ripe fruit of the medicine-food homologous plant from burseraceae family Olive Raeusch, with a polyphenol content of 200 mg/g, a lot number of OLE15-141001.

EXAMPLES 1 to 6

1. Preparation of the Total Extract of *Puerariae Lobatae Radix, Platycodonis Radix, Glycyrrhizae Radix ET Rhizoma, Siraitiae Fructus* and *Angelicae Dahuricae Radix*

(1) Compounding the decoction pieces of PUERARIAE LOBATAE RADIX, PLATYCODONIS RADIX, GLYCYR-RHIZAE RADIX ET RHIZOMA, SIRAITIAE FRUCTUS and ANGELICAE DAHURICAE RADIX (all of the decoction pieces are in line with the requirements set forth in *Chinese Pharmacopoeia* 2010 Edition) based on the weights shown in Table 1. After mixing, 10 times by weight of double distilled water was added and heated at 85° C. The materials were extracted for 60 minutes, filtered, and the filtrate was obtained;

(2) the filter cake was added with 10 times by weight of double distilled water, heated at 80° C., extracted for 60 minutes, filtered, and the filtrate was obtained;

(3) the two filtrates were combined and concentrated to give the total extract (i.e., concentrate). The soluble solid content in the total extract (the Brix) is 20~30%, 20° C.;

2. Preparation of the Composition Having Whitening and Brightening Effect (1) Preparation of the Compositions of Examples 1 to 6

According to the formulae in Table 1, the above-mentioned total extract was mixed with powder of *Osmanthus* and powder of Olive fruit, added with double distilled water, and made up to 50 ml. Among them, Example 5 was based on the components of Example 2 with white sugar added, which were finally formulated with double distilled water to reach 50 ml. Example 6 was based on the components of Example 2 with concentrated black currant juice (Guangdong Long He Biological technology co., LTD, Brix 64-66%, 20° C.) added, which were finally formulated with double distilled water to reach 50 ml.

TABLE 1

Formulae of the components of Examples 1 to 6

| Name of the raw materials | Example 1 | Example 2 | Example 3 | Example 4 | Example 5 | Example 6 |
| --- | --- | --- | --- | --- | --- | --- |
| PUERARIAE LOBATAE RADIX | 1 g | 2 g | 4 g | 5 g | 2 g | 2 g |
| PLATYCODONIS RADIX | 1 g | 1 g | 2 g | 2 g | 1 g | 1 g |
| GLYCYRRHIZAE RADIX ET RHIZOMA | 0.1 g | 0.5 g | 1 g | 1 g | 0.5 g | 0.5 g |
| SIRAITIAE FRUCTUS | 0.1 g | 0.5 g | 1 g | 2 g | 0.5 g | 0.5 g |
| ANGELICAE DAHURICAE RADIX | 0.1 g | 0.2 g | 0.5 g | 1 g | 0.2 g | 0.2 g |
| Powder of Osmanthus | 0.1 g | 0.3 g | 0.6 g | 1 g | 0.3 g | 0.3 g |
| Powder of Olive fruit | 0.01 g | 0.05 g | 0.05 g | 0.1 g | 0.05 g | 0.05 g |
| White suger | — | — | — | — | 3 g | — |
| Concentrated black currant juice | — | — | — | — | — | 1 g |

(2) Research Groups for Compounding

Also, in order to conduct better effect test on the compositions in the present Examples, part I, which is composed of powder of *Osmanthus* and powder of Olive fruit, as well as part II, which is composed of PUERARIAE LOBATAE RADIX, PLATYCODONIS RADIX, GLYCYRRHIZAE RADIX ET RHIZOMA, SIRAITIAE FRUCTUS and ANGELICAE DAHURICAE RADIX are established for carrying out the research on compounding. Among them, research groups for compounding are shown in Table 2. Among them, the preparation methods for the groups in Table 2 refer to the above-mentioned "(1) Preparation of the compositions of Examples 1 to 6".

TABLE 2

Design of research groups for compounding

| Number | Gropus | PUERARIAE LOBATAE RADIX (g) | PLATYCODONIS RADIX (g) | GLYCYRRHIZAE RADIX ET RHIZOMA (g) | SIRAITIAE FRUCTUS (g) | ANGELICAE DAHURICAE RADIX (g) | Powder of Osmanthus (g) | Powder of Olive fruit (g) | White suger (g) | Concentrated black currant juice (g) |
|---|---|---|---|---|---|---|---|---|---|---|
| 1 | Model group | — | — | — | — | — | — | — | — | — |
| 2 | part I-1 | — | — | — | — | — | 0.1 | 0.01 | — | — |
| 3 | part II-1 | 1 | 1 | 0.1 | 0.1 | 0.1 | — | — | — | — |
| 4 | Example 1 | 1 | 1 | 0.1 | 0.1 | 0.1 | 0.1 | 0.01 | — | — |
| 5 | part I-2 | — | — | — | — | — | 0.3 | 0.05 | — | — |
| 6 | part II-2 | 2 | 1 | 0.5 | 0.5 | 0.2 | — | — | — | — |
| 7 | Example 2 | 2 | 1 | 0.5 | 0.5 | 0.2 | 0.3 | 0.05 | — | — |
| 8 | part I-3 | — | — | — | — | — | 0.6 | 0.05 | — | — |
| 9 | part II-3 | 4 | 2 | 1 | 2 | 0.5 | — | — | — | — |
| 10 | Example 3 | 4 | 2 | 1 | 2 | 0.5 | 0.6 | 0.05 | — | — |
| 11 | part I-4 | — | — | — | — | — | 1 | 0.1 | — | — |
| 12 | part II-4 | 5 | 2 | 1 | 2 | 1 | — | — | — | — |
| 13 | Example 4 | 5 | 2 | 1 | 2 | 1 | 1 | 0.1 | — | — |
| 14 | Example 5 | 2 | 1 | 0.5 | 0.5 | 0.2 | 0.3 | 0.05 | 3 | — |
| 15 | Example 6 | 2 | 1 | 0.5 | 0.5 | 0.2 | 0.3 | 0.05 | — | 1 |

3. Detection of Polyphenols

In accordance with the "GBT 8313-2008 Detection method for the contents of tea polyphenols and catechins in tea leaves", groups in Table 2 were examined for polyphenols content, and the results are shown in Table 3.

TABLE 3

Polyphenols in research groups for compounding

| Number | Groups | Detected values of polyphenols (mg/100 ml) |
|---|---|---|
| 1 | Model group | 0 |
| 2 | part I-1 | 28 |
| 3 | part II-1 | 69 |
| 4 | Example 1 | 102 |
| 5 | part I-2 | 92 |
| 6 | part II-2 | 144 |
| 7 | Example 2 | 243 |
| 8 | part I-3 | 164 |
| 9 | part II-3 | 325 |
| 10 | Example 3 | 492 |
| 11 | part I-4 | 280 |
| 12 | part II-4 | 378 |
| 13 | Example 4 | 679 |
| 14 | Example 5 | 252 |
| 15 | Example 6 | 360 |

4. Animal Experiments—UVB Ultraviolet Radiation-Induced Skin Melanin Pigmentation Model in Guinea Pig (1) Pigment guinea pigs were purchased from Shanghai Jiagan Biological Technology Co., Ltd. Production license number: SCXK (Shanghai) 2010-0028, Use license number: SYXK (Shanghai) 2013-0087.

90 healthy female pigment guinea pigs were subjected to adaptive feeding for one week, then randomly divided into 15 groups according to body weight. Each group of animals were reared in the same cage, wherein the number of animals in each group is 6.

Instrument:

UVB ultraviolet radiometer, model: SH-4B; purchased from Shanghai Sigma high-tech Co., Ltd.

Colorimeter, Model: NH310; purchased from Shenzhen 3nh Technology Co., Ltd.

(2) Experimental Procedure

The guinea pigs were grouped according to Table 2 and then tested, with a total of 15 test groups. Test substances for each of the groups were extracted and formulated according to the relationship between the ratios set forth in Table 2.

Among these, group numbers 2, 5, 8, 11 in Table 2 (groups including part I): after mixing, the components were formulated to 50 ml with double distilled water.

After each raw materials of group numbers 3, 6, 9, 12 in Table 2 (groups including part II) were extracted in accordance with the relationship between the ratios, extracts were weighted according to the extraction yield, and were formulated to 50 ml with double distilled water.

After each raw materials as contents of part II in group numbers 4, 7, 10, 13 in Table 2 were extracted in accordance with the relationship between the ratios, extracts were weighted according to the extraction yield, and mixed with the materials as contents of part I in each of the groups, then formulated to 50 ml with double distilled water.

After each raw materials as contents of part II in group numbers 14, 15 in Table 2 were extracted in accordance with the relationship between the ratios, extracts were weighted according to the extraction yield, and mixed with the materials as contents of part I in each of the groups, added with white sugar or concentrated black currant juice, then formulated to 50 ml with double distilled water.

Conversion method for each dose group: human consumption amount is 50 ml/day, i.e. the human dose 0.83 ml/kg (according to 60 kg); after conversion to guinea pigs, the dosage is 3.75 ml/kg (the conversion factor is 4.5). The test substances were uniformly diluted in accordance with a gavage dose of 5 ml/kg, and then administrated by gavage.

The test groups were administrated with test samples on 9:00 to 11:00 a.m. every day, wherein all test substances were administered by oral gavage, and the model group was given the same volume of solvent. Administration was continued for 30 days, with a dosing volume of 5 ml/kg. Body weight was measured once for every five days and the doses were adjusted according to body weight.

The test substances were administered continuously for 30 days, and UVB irradiation was conducted on 3, 5, 7, 9 days after administration of the test substances. The irradiation dose is 200 mJ/cm$^2$ for a total of 4 times, and the total dose of 800 mJ/cm$^2$. The hairs on brown area of the back of all guinea pigs were shaved before irradiation, and the shaving area is 4 cm*4 cm.

All animals were photographed before irradiation and 30 days after administration of the test substances and measured for chromatic L values of skin area post irradiation. Statistics were conducted on L values before and after irradiation and change situations thereof, and comparisons were conducted among different groups and a group per se before and after irradiation. At the end of the experiment, parts of the skin under irradiation were fixed, and subjected to Fontana Masson staining.

Variations in L value (ΔL)=L value of the skin after irradiation−L value of the skin before irradiation The values were plotted using GraphPad Prism 5.0 medical drawing software, and SigmaStat software was used for data analysis. All data were represented by mean±standard deviation; as for Δ L, repeatedly measured two-way ANOVA was used, and SNK analytical test was used for group comparison.

Synergy is calculated according to the Jin's formula:

$q=E(A+B)/[EA+EB−EA*EB]$ where EA and EB are the effects of A and B when used alone; E (A+B) are the combined effect of the two.

q=0.85-1.15 denotes simple addition; 1.15<q<20 denotes enhancement; q>20 denotes obvious enhancement; q<0.56-0.85 denotes antagonism; q<0.55 denotes obvious antagonism.

(3) Results

The results of the effects on the reduction of brightness of guinea pig skin irradiated by ultraviolet are shown in Table 4.

TABLE 4

Effects of various formulae and Examples on the reduction of brightness of uguinea pig skin irradiated by ultraviolet (n = 6, $\bar{x} \pm S$)

| Groups | ΔL | Inhibitory rate (%) | Synergy coefficient q |
|---|---|---|---|
| Model group | −21.61 ± 3.03 | — | — |
| part I-1 | −16.52 ± 4.24 | 23.55 | 1.20 |
| part II-1 | −20.40 ± 2.73 | 5.60 | |
| Example 1 | −14.38 ± 2.59** | 33.46 | |
| part I-2 | −14.89 ± 2.19** | 31.09 | 1.43 |
| part II-2 | −20.88 ± 2.36 | 3.35 | |
| Example 2 | −11.28 ± 2.61** | 47.82 | |
| part I-3 | −13.82 ± 2.86** | 36.03 | 1.35 |
| part II-3 | −18.60 ± 1.41 | 13.93 | |
| Example 3 | −8.48 ± 1.43** | 60.76 | |
| part I-4 | −13.58 ± 4.59** | 37.14 | 1.54 |
| part II-4 | −17.30 ± 3.61 | 19.91 | |
| Example 4 | −5.12 ± 2.22** | 76.30 | |
| Example 5 | −11.88 ± 2.67** | 45.02 | — |
| Example 6 | −10.60 ± 1.76** | 50.96 | — |

**P < 0.01vs model group

In addition, q=0.85-1.15 denotes simple addition; 1.15<q<20 denotes enhancement; q>20 denotes obvious enhancement; q<0.56-0.85 denotes antagonism; q<0.55 denotes obvious antagonism.

Furthermore, after administration of test substances, animals of each of the groups do not have abnormal activities, and there were no differences in terms of body weight and weight gain.

Δ L+ represents partial white, Δ L− represents blackish, it can be seen that after UV irradiation, skin brightness of animals in model group was darkened.

In each of groups administrated with test substances, the inhibitory effect on reduction of skin brightness produced from contents of part I is stronger than that of part II.

In various groups of part I, the effect of the group part I-1 is the weakest, and each of the other groups of part I has very significant inhibitory effect on reduction of skin brightness (P<0.01, compared with model group).

In various groups of part II, only part II-4 has very significant inhibitory effect on reduction of skin brightness (P<0.01, compared with model group).

Example 1 has significant inhibitory effect on reduction of skin brightness (P<0.01, compared with model group), and inhibitory degree thereof is higher than that of part I-1 and part II-1, and there was a very significant difference (P<0.01) compared with part II-1. The synergy coefficient in the Example is 1.20, which denotes enhancement.

Example 2 has significant inhibitory effect on reduction of skin brightness (P<0.01, compared with model group), and inhibitory degree thereof is significantly higher than that of part I-2 (P<0.01) and part II-2 (P<0.01). The synergy coefficient in the Example is 1.43, which denotes enhancement.

Example 3 has significant inhibitory effect on reduction of skin brightness (P<0.01, compared with model group), and inhibitory degree thereof is significantly higher than that of part I-3 (P<0.01) and part II-3 (P<0.01). The synergy coefficient in the Example is 1.35, which denotes enhancement.

Example 4 has significant inhibitory effect on reduction of skin brightness (P<0.01, compared with model group), and inhibitory degree thereof is higher than that of part I-4 and part II-4, and there was a very significant difference (P<0.01) compared with part II-4. The synergy coefficient in the Example is 1.54, which denotes enhancement.

All of Examples 1 to 4 have very significant inhibitory effect on reduction of skin brightness (P<0.01, compared with model group). Polyphenol content in Examples 1 to 4 was detected to be in the range of 102-360 mg/100 ml.

All of the components which constitute part I and part II produce synergistic effect in terms of skin whitening and brightening function; the skin whitening and brightening effects of Examples 1 to 4 were significantly enhanced, and exert synergistic effects with part I and part II.

Example 5 and Example 6 were formed by adding white sugar or concentrated black currant juice to Example 2, which also have very significant inhibitory effect on reduction of skin brightness (P<0.01, compared with model group), and are comparable to Example 2 (P>0.05, compared with Example 2).

5. Cell Experiments

The reagents and instruments involved in the following cell experiments are as follows:

DMEM medium containing 10% fetal bovine serum, purchased from Biotech GmbH.

Mushroom tyrosinase, levodopa (L-DOPA) and thiazolyl blue tetrazolium bromide (MTT) were purchased from Sigma Corporation.

Arbutin (Sigma Corporation), microplate reader: multi-functional microplate reader (Thermo Company), $CO_2$ incubator (Nuaire, USA), inverted microscope (Leica, Germany), super-clean bench (Suzhou Purification Equipment Co., Ltd.), ultrasonic cell cracker (Scientz Biotechnology Company).

(I) Effect on Melanin Content in Melanoma Cells from B16 Mice,

The experiments were: melanoma cells from B16 mice (purchased from Shanghai Fuxiang Biotechnology Co., Ltd.) were adjusted with DMEM cell culture medium containing 10% fetal bovine serum, 100 U/mL penicillin and 100 U/mL streptomycin to reach a density of $1\times10^5$/mL, and were seeded into 6-well cell culture plates (3 mL per well). After cultured at 37° C., 5% $CO_2$ for 24 h, the test sample (Example 2) was added. After 3 days, the supernatant was discarded, and the cells were washed with PBS, then added with trypsin to degest the cells for 3 min (0.5 mL per well). Afterwards, 2 mL cell culture medium was added to terminate the digestion reaction, and cells of each group were counted. After centrifugation, the supernatant was discarded, and 0.5 mL of 1 mol/L NaOH solution was added. After vibrated for 1 h, a 1500 r/min centrifugation was conducted for 5 min. 200 μL was respectively taken and transferred to a 96-well cell culture plate, and tested for absorbance at 450 nm via a microplate reader to calculate the inhibitory rate for melanin synthesis. In the experiment, the control wells were added with the same volume amount of PBS as that of the sample. The positive control employs arbutin, at a concentration of 200 μM.

The inhibitory rate for melanin synthesis=[1−(A/B)/(C/D)]×100%.

A is the absorbance of the wells containing drug (i.e., sample wells or positive control wells), B is the number of cells in the wells containing drug, C the absorbance of the control wells, D is the number of cells in control wells.

The results of the effects of the test samples on melanin synthesis of melanoma cells from B16 mice are shown in Table 5.

TABLE 5

The effects of Example 2 on melanin synthesis of melanoma cells from B16 mice (n = 4, $\bar{x} \pm S$)

| Groups | Dilution times (times) | The inhibitory rate for melanin synthesis (%) |
|---|---|---|
| Arbutin | 200 μM | 46.70 ± 10.04 |
| Example 2 | Original liquor | 59.48 ± 9.72 |
|  | 2 | 55.34 ± 11.26 |
|  | 4 | 52.71 ± 6.65 |
|  | 8 | 45.56 ± 7.18 |
|  | 16 | 36.07 ± 10.44 |
|  | 32 | 28.62 ± 8.90 |
|  | 64 | 15.43 ± 4.83 |

It can be seen from Table 5 that the inhibitory effect of the composition in Example 2 on melanin synthesis of melanoma cells from B16 mice is reduced as the dilution times increase; its 8-fold dilution has an inhibitory rate for melanin synthesis of 45.56%, which is comparable to the inhibitory degree of 200 μM arbutin (P>0.05).

(II) Effects on Intracellular Tyrosinase Activity in Melanoma Cells from B16 Mice The experiments were: B16 melanin cells were adjusted with DMEM cell culture medium containing 10% fetal bovine serum, 100 U/mL penicillin and 100 U/mL streptomycin to reach a density of $1\times10^5$/mL, and were seeded into 6-well cell culture plates (3 mL per well). After cultured at 37° C., 5% $CO_2$ for 24 h, the test sample (Example 2) was added. After 3 days, the supernatant was discarded, and the cells were washed with PBS for twice. After each well was added 180 μL PBS solution containing 1% (v/v) Triton X-100, the cells were subjected to ultrasonication under ice bath, then each well was added 20 μL 10 mmol/L of L-DOPA, incubated at 37° C. for 60 min. A 1500 r/min centrifugation was conducted for 5 min. 100 μL was respectively taken and transferred to a 96-well cell culture plate, and tested for absorbance at 492 nm via a microplate reader to calculate the inhibitory rate for intracellular tyrosinase activity. The control wells were added with the same volume amount of PBS as that of the sample. The positive control employs arbutin, at an effect concentration of 200 μM.

Inhibition rate=(1−A/B)×100% wherein A is the mean absorbance of the wells containing drug (i.e., sample wells or positive control wells), B is the mean absorbance of the control wells.

The test results of Example 2 on intracellular tyrosinase activity in melanoma cells from B16 mice were shown in Table 6.

TABLE 6

Effects of Example 2 on intracellular tyrosinase activity in melanoma cells from B16 mice (n = 4, $\bar{x} \pm S$)

| Groups | Dilution times (times) | Inhibitory rate for tyrosinase activity (%) |
|---|---|---|
| Arbutin | 400 μM | 48.97 ± 9.44 |
| Example 2 | Original liquor | 54.29 ± 10.77 |
|  | 2 | 50.15 ± 6.71 |
|  | 4 | 46.64 ± 5.09 |
|  | 8 | 37.28 ± 11.23 |
|  | 16 | 28.35 ± 10.46 |
|  | 32 | 30.07 ± 7.05 |
|  | 64 | 19.53 ± 6.47 |

It can be seen from Table 6 that the inhibitory effect of the composition in Example 2 on melanin synthesis of melanoma cells from B16 mice is reduced as the dilution times increase; its 4-fold dilution has an inhibitory rate for melanin synthesis of 46.64%, which is comparable to the inhibitory degree of 400 μM arbutin (P>0.05).

Based on the above experiments, it was found that compounding the powder of *Osmanthus* and powder of Olive as well as and extracts of *PUERARIAE LOBATAE RADIX, PLATYCODONIS RADIX, GLYCYRRHIZAE RADIX ET RHIZOMA, SIRAITIAE FRUCTUS* and *ANGELICAE DAHURICAE RADIX* can produce a stronger whitening and brightening effect, i.e. produce synergy.

The Second Embodiment

1. Preparation of the total extract of *PUERARIAE LOBATAE RADIX, PLATYCODONIS RADIX, GLYCYRRHIZAE RADIX ET RHIZOMA, SIRAITIAE FRUCTUS* and *ANGELICAE DAHURICAE RADIX*

(1) Compounding the decoction pieces of *PUERARIAE LOBATAE RADIX, PLATYCODONIS RADIX, GLYCYRRHIZAE RADIX ET RHIZOMA, SIRAITIAE FRUCTUS* and *ANGELICAE DAHURICAE RADIX* (all of the decoction pieces are in line with the requirements set forth in Chinese Pharmacopoeia 2010 Edition) based on the weights shown in Table 7. After mixing, 12 times by weight of double distilled water was added and heated at 95° C. The materials were extracted for 80 minutes, filtered, and the filtrate was obtained;

(2) the filter cake was added with 15 times by weight of double distilled water, heated at 100° C., extracted for 90 minutes, filtered, and the filtrate was obtained;

(3) the two filtrates were combined and concentrated to give the total extract (i.e., concentrate). The soluble solid content in the total extract (the Brix) is 20~30% (percentage by weight), 20° C.; the total polyphenols in the total extract are ≥500 mg/100 ml.

The powder of *Osmanthus* is a solid prepared from aqueous extraction of dried flowers of the edible *Osmanthus*, with a polyphenol content of 140 mg/g.

The powder of Olive fruit is a solid prepared from alcoholic extraction (58 v/v % enthanol) of the dry ripe fruit of the medicine-food homologous plant from burseraceae family Olive Raeusch, with a polyphenol content of 190 mg/g.

2. Preparation of the Composition

1) According to the formulae in Table 7, the above-mentioned total extract of *PUERARIAE LOBATAE RADIX, PLATYCODONIS RADIX, GLYCYRRHIZAE RADIX ET RHIZOMA, SIRAITIAE FRUCTUS* and *ANGELICAE DAHURICAE RADIX* was mixed with other components in the formulae, added with double distilled water, and made up to 50 ml.

Or 2) According to the formulae in Table 7, after the above-mentioned total extract of *PUERARIAE LOBATAE RADIX, PLATYCODONIS RADIX, GLYCYRRHIZAE RADIX ET RHIZOMA, SIRAITIAE FRUCTUS* and *ANGELICAE DAHURICAE RADIX* was mixed with other components in the formulae, excipients (various excipients for formulations for oral administration, except for water as mentioned above) were added to prepare corresponding oral preparations (a type of food), wherein the oral preparations may be in the forms of beverages, instant granules or candies.

The Third Embodiment

1. Preparation of the Total Extract of *Puerariae Lobatae Radix, Platycodonis Radix, Glycyrrhizae Radix ET Rhizoma, Siraitiae Fructus* and *Angelicae Dahuricae Radix*

(1) Compounding the decoction pieces of *PUERARIAE LOBATAE RADIX, PLATYCODONIS RADIX, GLYCYRRHIZAE RADIX ET RHIZOMA, SIRAITIAE FRUCTUS* and

TABLE 7

| | | | Formulae | | | | |
|---|---|---|---|---|---|---|---|
| | Name | | Example 7 | Example 8 | Example 9 | Example 10 | Example 11 |
| Mass (g) | *PUERARIAE LOBATAE* RADIX | | 15 | 25 | 30 | 35 | 45 |
| | *PLATYCODONIS* RADIX | | 11 | 12 | 14 | 16 | 18 |
| | *GLYCYRRHIZAE* RADIX ET RHIZOMA | | 2 | 4 | 6 | 8 | 7 |
| | *SIRAITIAE FRUCTUS* | | 2 | 4 | 8 | 12 | 15 |
| | *ANGELICAE DAHURICAE* RADIX | | 3 | 6 | 7 | 8 | 9 |
| | Powder of *Osmanthus* | | 2 | 5 | 7 | 8 | 9 |
| | Powder of Olive fruit | | 0.2 | 0.6 | 0.7 | 0.8 | 0.9 |
| | Food ingredients | non-dairy creamer | | | 0.5 | | 5 |
| | | malt dextrin | | | 0.5 | | 5 |
| | | instant tea powder | | | | | 5 |
| | Food additives | Potassium citrate | 0.1 | | 1 | | 0.5 |
| | | vitamin C | | | 1 | | 0.8 |
| | Fruit Juice | apple juice | | | | 25 | 5 |
| | | orange juice | | | | | 10 |
| | Fruit powder | mango fruit powder | | 10 | | 25 | 20 |
| | | mulberry fruit powder | | | | 25 | 10 |

ANGELICAE DAHURICAE RADIX (all of the decoction pieces are in line with the requirements set forth in Chinese Pharmacopoeia 2010 Edition) based on the weights shown in Table 8. After mixing, 20 times by weight of double distilled water was added and heated at 100° C. The materials were extracted for 100 minutes, filtered, and the filtrate was obtained;

(2) the filter cake was added with 10 times by weight of double distilled water, heated at 90° C., extracted for 80 minutes, filtered, and the filtrate was obtained;

(3) the two filtrates were combined and concentrated and dried to give the solid total extract (extract powder). The total polyphenols in the solid total extract are ≥25 mg/g.

TABLE 8

Formulae

| | Name | | Example 12 | Example 13 | Example 14 | Example 15 | Example 16 |
|---|---|---|---|---|---|---|---|
| Mass (g) | PUERARIAE LOBATAE RADIX | | 10 | 20 | 30 | 40 | 50 |
| | PLATYCODONIS RADIX | | 10 | 13 | 15 | 17 | 19 |
| | GLYCYRRHIZAE RADIX ET RHIZOMA | | 1 | 3 | 5 | 9 | 10 |
| | SIRAITIAE FRUCTUS | | 3 | 5 | 9 | 13 | 17 |
| | ANGELICAE DAHURICAE RADIX | | 2 | 5 | 7 | 8 | 9 |
| | Concentrate of Osmanthus extract | | 1 | 4 | 6 | 8 | 10 |
| | Concentrate of Olive fruit extract | | 0.2 | 0.4 | 0.5 | 0.9 | 1.0 |
| | Food ingredients | White suger | | | 0.3 | | 3 |
| | | malt dextrin | | | 0.5 | | 5 |
| | | instant tea powder | | | | | 5 |
| | Food additives | Sodium citrate | 0.1 | | 1 | | 0.5 |
| | | stevioside | | 0.1 | | | 0.2 |
| | | vitamin E | | | 1 | | 0.6 |
| | Fruit Juice | apple juice | | | | | 8 |
| | | grape juice | | | | 15 | 20 |
| | Fruit powder | Apple fruit powder | 15 | | 20 | | 22 |
| | | mulberry fruit powder | | 21 | | | 12 |

The concentrate of Osmanthus extract is a concentrate of Osmanthus extract prepared from aqueous extraction of dried flowers of the edible Osmanthus followed by concentration, with a polyphenol content of 6000 mg/100 ml.

The concentrate of Olive fruit extract is a concentrate prepared from aqueous extraction of the dry ripe fruit of the medicine-food homologous plant from burseraceae family Olive Raeusch followed by concentration, with a polyphenol content of 8000 mg/100 ml.

2. Preparation of the Composition

1) According to the formulae in Table 8, the above-mentioned solid total extract (extract powder) of PUERARIAE LOBATAE RADIX, PLATYCODONIS RADIX, GLYCYRRHIZAE RADIX ET RHIZOMA, SIRAITIAE FRUCTUS and ANGELICAE DAHURICAE RADIX was mixed with other components in the formulae, added with double distilled water, and made up to 50 ml.

Or 2) According to the formulae in Table 8, after the above-mentioned solid total extract (extract powder) of PUERARIAE LOBATAE RADIX, PLATYCODONIS RADIX, GLYCYRRHIZAE RADIX ET RHIZOMA, SIRAITIAE FRUCTUS and ANGELICAE DAHURICAE RADIX was mixed with other components in the formulae, excipients (various excipients for formulations for oral administration, except for water as mentioned above) were added to prepare corresponding oral preparations (a type of food), wherein the oral preparations may be in the forms of beverages, instant granules or candies.

The above embodiments are the preferred embodiments of the present invention. It should be noted that, for a person having ordinary skill in the art, several improvements and modifications may be made without departing from the principles of the present invention, and these improvements and modifications should be regarded as within the scope claimed by the invention.

The invention claimed is:

1. A composition having whitening and brightening effects, comprising parts by weight of 1 part to 10 parts of Osmanthus, 0.1 parts to 1 part of Canarium album Raeusch, 10 parts to 50 parts of PUERARIAE LOBATAE RADIX, 10 parts to 20 parts of PLATYCODONIS RADIX, 1 part to 10 parts of GLYCYRRHIZAE RADIX ET RHIZOMA, 1 part to 20 parts of SIRAITIAE FRUCTUS, 1 part to 10 parts of ANGELICAE DAHURICAE RADIX.

2. The composition as claimed in claim 1, characterized in that: the ingredients of Canarium album Raeusch and Osmanthus in the composition are dried powder of juice or extract, or original liquor of juice or extract, concentrate of juice or extract or enriched material of active ingredients;

the *PUERARIAE LOBATAE RADIX, PLATYCODONIS RADIX, GLYCYRRHIZAE RADIX ET RHIZOMA, SIRAITIAE FRUCTUS* and *ANGELICAE DAHURICAE RADIX* are in the form of crude drugs or dried powder, or concentrate of extract or said enriched material of active ingredients.

3. The composition as claimed in claim 1, characterized in that: the total extract of *PUERARIAE LOBATAE RADIX, PLATYCODONIS RADIX, GLYCYRRHIZAE RADIX ET RHIZOMA, SIRAITIAE FRUCTUS* and *ANGELICAE DAHURICAE RADIX* includes: the extract obtained by mixing *PUERARIAE LOBATAE RADIX, PLATYCODONIS RADIX, GLYCYRRHIZAE RADIX ET RHIZOMA, SIRAITIAE FRUCTUS* and *ANGELICAE DAHURICAE RADIX* with water or alcohol.

4. The composition as claimed in claim 1, characterized in that: the composition further comprises: one or more of a food ingredient, a food additive or a fruit powder.

5. The composition as claimed in claim 4, characterized in that: the food ingredient includes: one or more of white sugar, non-dairy creamer, malt dextrin, and/or tea powder; wherein the weight ratio of food ingredients to Osmanthus is 1-50: 1-10;
the food additive includes: one or more of citric acid and sodium salt or potassium salt thereof, vitamin C, vitamin E, and/or stevioside; wherein the weight ratio of food additives to Osmanthus is 0.1-2: 1-10;
the fruit powder includes: one or more of apple fruit powder, grape fruit powder, black currant fruit powder, mango fruit powder, and/or mulberry fruit powder; wherein the weight ratio of fruit powder to Osmanthus is 10-50: 1-10.

6. A method for preparing the composition as claimed in claim 1, characterized in that: it comprises:
mixing the *Osmanthus, Canarium album Raeusch* and *PUERARIAE LOBATAE RADIX, PLATYCODONIS RADIX, GLYCYRRHIZAE RADIX ET RHIZOMA, SIRAITIAE FRUCTUS* and *ANGELICAE DAHURICAE RADIX*, and then preparing them into the composition.

7. The method as claimed in claim 6, characterized in that: the composition is an oral dosage form;
in the process of preparing the composition, one or more of food ingredients, food additives, and/or fruit powder as claimed in claim 6 are further added.

8. A method for preparing food or health product having whitening and brightening effect, comprising formulating the composition as claimed in claim 1 as a food product or medicament.

9. The method as claimed in claim 8, characterized in that: the food or health product includes: a liquid food or health product, or solid, semi-solid food or health product;
wherein the liquid food or health product includes: beverages, oral liquid or milk; the solid or semi-solid food or health product includes: biscuits, pastries, instant granules, candies, chocolates, jelly, jam, canned food, or gels.

10. The composition as claimed in claim 1, further comprises fruit juice.

11. The composition as claimed in claim 10, characterized in that, the fruit juice includes: one or more of apple juice, grape juice, black currant juice, sugar cane juice, and/or orange juice; or one or more of concentrated apple juice, concentrated grape juice, concentrated black currant juice, concentrated sugarcane juice, and/or concentrated orange juice; the weight ratio of the fruit juice to Osmanthus is 10-50 : 1-10.

* * * * *

UNITED STATES PATENT AND TRADEMARK OFFICE
CERTIFICATE OF CORRECTION

PATENT NO. : 10,098,372 B2
APPLICATION NO. : 15/126054
DATED : October 16, 2018
INVENTOR(S) : Shuo Liu et al.

It is certified that error appears in the above-identified patent and that said Letters Patent is hereby corrected as shown below:

In the Claims

In Claim 7, Column 20, Line 10, delete "claim 6" and insert --claim 4-- therefor.

Signed and Sealed this
Eleventh Day of December, 2018

Andrei Iancu
*Director of the United States Patent and Trademark Office*